United States Patent
Cazer et al.

(10) Patent No.: US 6,410,520 B2
(45) Date of Patent: Jun. 25, 2002

(54) SELECTIVE CRYSTALLIZATION OF 3-PYRIDYL-1-HYDROXYETHYLIDENE-1, 1-BISPHOSPHONIC ACID SODIUM AS THE HEMIPENTAHYDRATE OR MONOHYDRATE

(75) Inventors: Frederick Dana Cazer, Earlville, NY (US); Gregory Eugene Parry, Lawrenceville, NJ (US); Dennis Michael Billings, Norwich; Nancy Lee Redman-Furey, Smyrna, both of NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/771,825

(22) Filed: Jan. 29, 2001

Related U.S. Application Data

(60) Provisional application No. 60/179,505, filed on Feb. 1, 2000.

(51) Int. Cl.$^7$ ................. A61K 31/663; A61K 31/4406; C07D 213/24
(52) U.S. Cl. ........................................ 514/89; 546/22
(58) Field of Search ..................... 514/89, 277; 546/22

(56) References Cited

U.S. PATENT DOCUMENTS

| | | | |
|---|---|---|---|
| 4,054,598 A | 10/1977 | Blum et al. |
| 4,267,108 A | 5/1981 | Blum et al. |
| 4,304,734 A | 12/1981 | Jary et al. |
| 4,327,039 A | 4/1982 | Blum et al. |
| 4,330,537 A | 5/1982 | Francis |
| 4,407,761 A | 10/1983 | Blum et al. |
| 4,447,256 A | 5/1984 | Suzuki et al. |
| 4,621,077 A | 11/1986 | Rosini et al. |
| 4,705,651 A | 11/1987 | Staibano |
| 4,719,203 A | 1/1988 | Bosies et al. |
| 4,777,163 A | 10/1988 | Bosies et al. |
| 4,812,316 A | 3/1989 | Rossi et al. |
| 4,927,814 A | 5/1990 | Gall et al. |
| 4,939,130 A | 7/1990 | Jaeggi et al. |
| 4,942,157 A | 7/1990 | Gall et al. |
| 5,002,937 A | 3/1991 | Bosies et al. |
| 5,035,898 A | 7/1991 | Chang et al. |
| 5,039,819 A | 8/1991 | Kieczykowski |
| 5,049,663 A | 9/1991 | Terada et al. |
| 5,068,440 A | 11/1991 | Jeffery et al. |
| 5,091,525 A | 2/1992 | Brennan |
| 5,110,807 A | 5/1992 | Jaeggi |
| 5,206,253 A | 4/1993 | Bosies et al. |
| 5,312,925 A | 5/1994 | Allen et al. |
| 5,317,015 A | 5/1994 | Ullrich et al. |
| 5,354,760 A | 10/1994 | Petersen et al. |
| 5,405,994 A | 4/1995 | Bonnery et al. |
| 5,480,875 A | 1/1996 | Isomura et al. |
| 5,525,354 A | 6/1996 | Posti et al. |
| 5,545,737 A | 8/1996 | Sato et al. |
| 5,580,977 A | 12/1996 | Henning et al. |
| 5,583,122 A | 12/1996 | Benedict et al. |
| 5,602,115 A | 2/1997 | Nugent |
| 5,760,009 A | 6/1998 | Allen et al. |

FOREIGN PATENT DOCUMENTS

| | | |
|---|---|---|
| BE | 1000075 A | 2/1988 |
| EP | 0082472 B1 | 7/1986 |
| EP | 252505 A | 1/1988 |
| EP | 0494844 A1 | 7/1992 |
| GB | 2316945 A | 3/1998 |
| HU | 206726 B | 12/1992 |
| JP | 5598193 C | 7/1980 |
| WO | WO 95/06052 A1 | 3/1995 |
| WO | WO 96/33199 A1 | 10/1996 |

OTHER PUBLICATIONS

Nicholson et al., "A General Method of Preparation of Tetramethyl Alkyl–1–hydroxy–1,1–diphosphonates", *J. Of Organic Chem.*, vol. 36, pp. 3843–3845, 1971.

Ebetino et al., "Elucidation of a Pharmacophore for the Bisphosphonate Mechanism of Bone Antiresorptive Activity", *Phosphorus, Sulfur, and Silicon*, vol. 109–110, pp. 217–220, 1996.

Ebetino et al., "Recent Work on the Synthesis of Phosphonate–Containing, Bone–Active Heterocycles", *Heterocycles*, vol. 30, No. 2, pp. 855–862, 1990.

*Primary Examiner*—Charanjit S. Aulakh
(74) *Attorney, Agent, or Firm*—Mary Pat McMahon; James C. Kellerman; David V. Upite

(57) ABSTRACT

The present invention discloses 3-pyridyl-1-hydroxyethylidene-1,1-bisphosphonic acid sodium hemipentahydrate and monohydrate, methods of preparing the hemipentahydrate or monohydrate through control of the nucleation temperature and rate of crystallization and pharmaceutical compositions containing one or both of the hydrate forms.

18 Claims, No Drawings

SELECTIVE CRYSTALLIZATION OF 3-PYRIDYL-1-HYDROXYETHYLIDENE-1, 1-BISPHOSPHONIC ACID SODIUM AS THE HEMIPENTAHYDRATE OR MONOHYDRATE

CROSS REFERENCE

This application claims priority under Title 35, United States Code 119(e) from Provisional Application Ser. No. 60/179,505, filed Feb. 1, 2000.

TECHNICAL FIELD

The present invention relates to 3-pyridyl-1-hydroxyethylidene-1,1-bisphosphonic acid sodium hemipentahydrate and monohydrate, compositions containing said hemipentahydrate and/or monohydrate and methods of selective crystallization of the hemipentahydrate or monohydrate.

BACKGROUND OF THE INVENTION

Bisphosphonates such as 3-pyridyl-1-hydroxyethylidene-1,1-bisphosphonic acid (RISEDRONATE) have been proposed for use in the treatment of diseases of bone and calcium metabolism. Such diseases include osteoporosis, hyperparathyroidism, hypercalcemia of malignancy, ostolytic bone metastases, myosistis ossifcans progressiva, calcinoisis universalis, arthritis, neuritis, bursitis, tendonitis and other inflammatory conditions. Paget's disease and heterotropic ossification are currently successfully treated with both EHDP (ethane-1-hydroxy-1,1-diphosphonic acid) and RISEDRONATE.

The bisphosphonates tend to inhibit the resorption of bone tissue, which is beneficial to patients suffering from excessive bone loss. However, in spite of certain analogies in biological activity, all bisphosphonates do not exhibit the same degree of biological activity. Some bisphosphonates have serious drawbacks with respect to the degree of toxicity in animals and the tolerability or negative side effects in humans. The salt and hydrate forms of bisphosphonates alter both their solubility and their bioavailability.

It is known in the literature that some bisphosphonic acids and their salts are capable of forming hydrates, risedronate sodium exists in three hydration states: mono, hemipenta and anhydrous. Crystallization procedures which selectively yield the hemipentahydrate form or the monohydrate form are desirable. This application describes the hemipentahydrate and the monohydrate crystal forms, the compositions containing said hemipentahydrate and monohydrate crystal forms and selective formation of these crystals.

SUMMARY OF THE INVENTION

The present invention discloses 3-pyridyl-1-hydroxyethylidene-1,1-bisphosphonic acid sodium hemipentahydrate and monohydrate, compositions containing said hemipentahydrate and/or monohydrate and methods of selective crystallization of the hemipentahydrate or monohydrate. The temperature of nucleation and the rate of crystallization are the critical variables that control the ratio of hydrates formed.

DETAILED DESCRIPTION OF THE PRESENT INVENTION

The present invention is directed to a 3-pyridyl-1-hydroxyethylidene-1,1-bisphosphonic acid sodium hemipentahydrate and monohydrate and compositions containing said hemipentahydrate and monohydrate. A novel process is also disclosed for the selective crystallization of the geminal bisphosphonate, risedronate sodium, 3-pyridyl-1-hydroxyethylidene-1,1-bisphosphonic acid sodium as the hemipentahydrate and as the monohydrate.

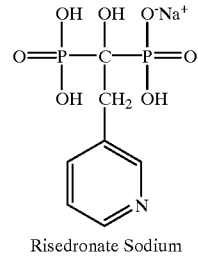

Risedronate Sodium

Risedronate sodium, the mono sodium salt of risedronate, exists in three crystalline hydration states: anhydrous, mono and hemipentahydrate. The monohydrate and hemipentahydrate are preferred.

The hemipentahydrate is the thermodynamically preferred crystalline form under typical processing conditions based on the observation that monohydrate crystals converted to the hemipentahydrate form.

The monohydrate is by weight of water from about 5.0% to about 7.1%, more preferably from about 5.6% to about 6.5% and most preferably about 5.6%. The monohydrate is further characterized by single crystal X-ray crystallography, and thermogravimetric analysis. The monohydrate form also exhibits identifiable signatures when examined by X-ray powder diffraction, differential scanning calorimetry, Fourier transform infrared spectroscopy or near infrared spectroscopy.

The hemipentahydrate is by weight of water from about 11.9% to about 13.9%, more preferably from about 12.5% to about 13.2% and most preferably about 12.9%. The hemipentahydrate is further characterized by single crystal X-ray crystallography, and thermogravimetric analysis. The hemipentahydrate form also exhibits identifiable signatures when examined by X-ray powder diffraction, differential scanning calorimetry, Fourier transform infrared spectroscopy or near infrared spectroscopy.

The temperature of nucleation and the rate of crystallization are the critical variables that control the ratio of hydrates formed. The nucleation temperature can be controlled by controlling the ratio of water to solute, the solution temperature, and the ratio of organic solvent to water.

The risedronate sodium hemipentahydrate is the thermodynamically favored form under the typical processing conditions described. Compositions comprise by weight of risedronate sodium hydrate from about 50% to about 100%, more preferably from about 80% to about 100%, most preferably from about 90% to about 100% risedronate sodium hemipentahydrate and from about 50% to about 0%, more preferably from about 20% to about 0%, most preferably from about 10% to about 0% risedronate sodium monohydrate.

Altering the processing conditions as described can selectively produce the monohydrate crystal form. Compositions comprise by weight of risedronate sodium hydrate from about 50% to about 99%, more preferably from about 80% to about 99%, most preferably from about 95% to about 99% risedronate sodium monohydrate and from about 50% to about 1%, more preferably from about 20% to about 1%, most preferably from about 5% to about 1% risedronate sodium hemipentahydrate.

The invention further comprises pharmaceutical compositions containing the hemipentahydrate and monohydrate compounds.

DEFINITIONS AND USAGE OF TERMS

The following is a list of definitions for terms used herein:

The term "risedronate", as used herein, denotes 3-pyridyl-1-hydroxyethylidene-1,1-bisphosphonic acid and has the following structure:

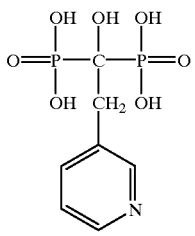

The compound risedronate is further described in U.S. Pat. No. 5,583,122, Benedict et al., assigned to the Procter & Gamble Co., issued Dec. 10, 1996, and "An American Conference, Bisphosphonates: Current Status and future Prospects," The Royal College of Physicians, London, England, May 21–22, 1990, organized by IBC Technical Services, both references hereby are incorporated by reference.

As used herein, "solvent", is a substance capable of dissolving another substance to form a uniform solution. The solvent may either be polar or non-polar. Solvents are selected from the group consisting of alcohols, esters, ethers, ketones, amides, and nitriles. Most preferred is isopropanol.

The Process

The process according to the present invention is characterized in that the process described herein is readily adapted to industrial production. The following non-limiting examples illustrate the processes of the present invention.

The extent of hydration 3-pyridyl-1-hydroxyethylidene-1,1-bisphosphonic acid sodium can be controlled by varying the crystallization parameters to control the temperature of nucleation and rate of crystallization. The ratio of hemipentahydrate to monohydrate crystal forms in the product can be effectively controlled by varying the water to 3-pyridyl-1-hydroxyethylidene-1,1-bisphosphonic acid sodium ratio and the isopropanol to water ratio as well as the temperature (see below).

General Procedure

An aqueous solution of 3-pyridyl-1-hydroxyethylidene-1,1-bisphosphonic acid sodium at 0–75° C., preferably 25–75° C., more preferably 45–75° C. will selectively yield either the monohydrate or the hemipentahydrate crystal forms depending upon the conditions of crystallization. The temperature of nucleation and the rate of crystallization governs the hydrate, varying the ratio of water: isopropanol and varying temperature and cooling ramp of the aqueous solution control the ratios of the hydration states formed.

Table 1 shows eight examples of reaction conditions which selectively produce 3-pyridyl-1-hydroxyethylidene-1,1-bisphosphonic acid sodium containing varying hemipenta to monohydrate ratios. The theoretical moisture level for the monohydrate is 5.6% and for the hemipentahydrate is 12.9%.

TABLE 1

| Example | Weight of Water (X = weight of compound 2) | Weight of isopropanol | IPA Addition Temp (° C.) | Cooling Ramp (° C.) | % H2O KF |
|---|---|---|---|---|---|
| 1 | 8.72X | 2.94X | 70 | 70 hold | 5.7 |
| 2 | 22X | 160X@0° C. | 70 | 70–0 in 2 min. Quench | 5.9 |
| 3 | 7.2X | 1.08X | 75 | 75–60 in 4 hrs 60–25 in 2 hrs. | 9.6 |
| 4 | 9X | 1.26X | 75 | 75–60 in 4 hrs 60–25 in 2 hrs | 11.4 |
| 5 | 8.2X | 0.9X | 60 | 60 hold 4 hrs. 60–25 in 2 hrs. | 12.3 |
| 6 | 9.5X | 1.05X | 60 | 60–25 in 2 hrs | 13.0 |
| 7 | 8.2X | 1.39X | 60 | 60 hold 4 hrs. 60–25 in 2 hrs. | 13.0 |
| 8 | 8.2X | 1.15X | 60 | 60–25 in 2 hrs | 13.1 |

EXAMPLE 1

Hemipentahydrate

Conditions leading to nucleation between 25–70° C., preferably 50–70° C. with a cooling ramp of 0.1–5° C. per minute, preferably 0.1–2° C. per minute produce the hemipentahydrate. The hemipentahydrate is formed by suspending 3-pyridyl-1-hydroxyethylidene-1,1-bisphosphonic acid n water at about 60° C., adjusting the pH to 4.7–5.0 with sodium hydroxide, adding isopropanol to the resulting solution, cooling the suspension and collecting the product by filtration.

EXAMPLE 2

Monohydrate

Conditions leading to nucleation above 45° C., preferably above 55° C. with appropriate time at temperature and without a cooling ramp or with a rapid quench produce the monohydrate. Maintaining the aqueous solution of 3-pyridyl-1-hydroxyethylidene-1,1-bisphosphonic acid sodium at 70° C., the monohydrate slowly crystallizes and is isolated by filtration of the crystals from the hot solution. Conversely, quenching of the 70° C. aqueous solution directly into 0° C. isopropanol also yields the crystalline monohydrate.

Compositions

The compounds made herein may be used in pharmaceutical compositions. The term "pharmaceutical composition" means a dosage form comprised of a safe and effective amount of an active ingredient and pharmaceutically-acceptable excipients. The pharmaceutical compositions described herein are comprised of from about, 0.1% to about 99%, preferably from about 0.5% to about 95% of a bisphosphonate active ingredient, and from about 1% to about 99.9%, preferably from 5.00% to about 99.90% of pharmaceutically-acceptable excipients. For risedronate sodium monohydrate or hemipentahydrate, an oral composition comprises, preferably 0.25% to 40%, preferably from about 0.5% to about 30% of a risedronate active ingredient and from about 60% to about 97%, preferably from about 70% to about 99.5% of pharmaceutically-acceptable excipients.

The phrase "safe and effective amount", as used herein means an amount of a compound or composition high enough to significantly positively modify the symptoms and/or condition to be treated, but low enough to avoid serious side effects (at a reasonable benefit/risk ratio), within the scope of sound medical judgment. The safe and effective amount of active ingredient for use in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "risedronate active ingredient" includes the risedronate, risedronate salts, and risedronate esters or any mixture thereof. Any pharmaceutically-acceptable, non-toxic salt or ester of risedronate may be used as the risedronate active ingredient in the dosage forms of the present invention. The salts of risedronate may be acid addition salts, in particular for risedronate the hydrochloride, but any pharmaceutically-acceptable, non-toxic organic or inorganic acid salt may be used. In addition, salts formed with the phosphonic acid group may be used, including, but not limited to alkali metal salts (K, Na) and alkaline earth metal salts (Ca, Mg) the Ca and Na salts being preferred.

Particularly, other esters of bisphosphonate which are suitable for use as the active ingredient herein are straight chain or branched chain $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl, esters, including but not limited to vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl ester, including, but not limited to phenyl, toluyl, xylyl, and naphthyl; alicyclic esters, including, but not limited to, menthyl; and aralkyl esters, including, but not limited to benzyl, and phenethyl.

The term "pharmaceutically-acceptable excipients" as used herein includes any physiologically inert, pharmacologically inactive material known to one skilled in the art, which is compatible with the physical and chemical characteristics of the particular active ingredient selected for use. Pharmaceutically-acceptable excipients include, but are not limited to, polymers, resins, plasticizers, fillers, lubricants, binders, disintegrants, solvents, co-solvents, buffer systems, surfactants, preservatives, sweetening agents, flavoring agents, pharmaceutical grade dyes and pigments. All or part of the pharmaceutically-acceptable excipients contained in the pharmaceutical compositions described herein is used to make the film coating which is to be utilized in the novel oral dosage forms described herein.

The term "oral dosage form" as used herein means any pharmaceutical composition intended to be administer to the stomach of an individual via the mouth of said individual As stated hereinabove, pharmaceutically-acceptable excipients include, but are not limited to polymers, resins, plasticizers, fillers, lubricants, binders, disintegrants, solvents, co-solvents, surfactants, preservatives, sweetener agents, flavoring agents, buffer systems, pharmaceutical-grade dyes and pigments.

The preferred solvent is water.

Flavoring agents among those useful herein include those described in *Remington's Pharmaceutical Sciences,* 18th Edition, Mack Publishing Company, 1990, pp. 1288–1300, incorporated by reference herein. Dyes, or pigments among those useful herein include those described in *Handbook of Pharmaceutical Excipients,* Second Edition pp. 126–134, 1994 by the American Pharmaceutical Association & the Pharmaceutical Press, incorporated by reference herein.

Preferred co-solvents include, but are not limited to, ethanol, glycerin, propylene glycol, polyethylene glycol.

Preferred buffer systems include, but are not limited to potassium acetate, boric carbonic, phosphoric, succinic, malic, tartaric, citric, acetic, benzoic, lactic, glyceric, gluconic, glutaric and glutamic. Particularly preferred are phosphoric, tartaric, citric, and potassium acetate.

Preferred surfactants include, but are not limited to, polyoxyethylene sorbitan fatty acid esters, polyoxyethylene monoalkyl ethers, sucrose monoesters and lanolin esters and ethers.

Preferred preservatives include, but are not limited to, phenol, alkyl esters of parahydroxybenzoic acid, benzoic acid and the salts thereof, boric acid and the salts thereof, sorbic acid and the salts thereof, chorbutanol, benzyl alcohol, thimerosal, nitromersol, benzalkonium chloride, cetylpyridinium chloride, methyl paraben, and propyl paraben. Particularly preferred are the salts of benzoic acid, cetylpyridinium chloride, methyl paraben and propyl paraben.

Preferred sweeteners include, but are not limited to, sucrose, glucose, saccharin, and aspartame. Particularly preferred are sucrose and saccharin.

Preferred binders include, but are not limited to methycellulose, sodium carboxymethycellulose, hydroxypropylmethylcellulose, carbomer, povidone, acacia, guar gum, xanthan gum and tragacanth. Particularly preferred are methycellulose, carbomer, xanthan gum, guar gum, povidone and sodium carboxymethycellulose.

Preferred fillers include, but are not limited to lactose, sucrose, maltodextrin, mannitol, starch, and microcrystalline cellulose.

Preferred plasticizers include, but are not limited to polyethylene glycol, propylene glycol, dibutyl phthalate, and castor oil, acetylated monoglycerides, and triacetin.

Preferred lubricants include, but are not limited to, magnesium stearate, stearic acid, and talc.

Preferred disintegrants include, but are not limited to, crospovidone, sodium carboxymethyl starch, sodium starch glycolate, sodium carboxymethyl cellulose, alginic acid, clays, and ion exchange resins.

Preferred polymers, include but are not limited to hydroxypropylmethylcellulose (HPMC) alone and/or in combination with hydroxypropylcellulose (HPC), carboxymethylcellulose, acrylic resins such as Eudragit® RL30D, manufactured by Rohm Pharma GmbH Weiderstadt, West Germany, methylcellulose, ethylcellulose, and polyvinylpyrrolidone or other commercially available film-coating preparations such as Dri-Klear, manufactured by Crompton & Knowles Corp., Mahwah, N.J. or Opadry manufactured by Colorcon, West Point, Pa.

Other formulations which may be used to administer the bisphosphonate active ingredient. Such formulations include but are not limited to gel formulations as disclosed in WO97/29754 and EP 0 407 344; effervescent formulations as disclosed in WO97/44017; iontophoretic formulations as disclosed in U.S. Pat. No. 5,730,715; and transdermal formulations as disclosed in EP 0 407 345.

The compositions of the present invention allow for greater flexibility in dosage administration and dosing intervals. For example, the compositions of the present invention may be dosed daily, weekly, biweekly or monthly. The safe and effective amount will vary with the particular condition being treated, the age and physical condition of the patient being treated, the severity of the condition, the duration of treatment, and the nature of concurrent therapy.

What is claimed is:

1. A process for selectively producing 3-pyridyl-1-hydroxyethlidene-1,1-bisphosphonic acid sodium hemipentahydrate and monohydrate comprising the steps of:
   a) providing an aqueous solution of 3-pyridyl-1-hydroxyethlidene-1,1-bisphosphonic acid sodium;
   b) heating the aqueous solution to a temperature from about 45° C. to about 75° C.;
   c) adding a solvent to the aqueous solution; and
   d) optionally cooling the aqueous solution.

2. The process of claim 1 wherein the solvent is selected from the group consisting of alcohols, esters, ethers, ketones, amides, and nitrites.

3. The process of claim 2 wherein the aqueous solution is heated to a temperature from about 55° C. to about 75° C.

4. The process of claim 2 wherein the aqueous solution is heated to about 70° C.

5. The process of claim 4 wherein the aqueous solution is not cooled.

6. The process of claim 5 wherein the solvent is isopropanol.

7. The process of claim 2 wherein the aqueous solution is heated to a temperature from about 50° C. to about 70° C.

8. The process of claim 7 wherein the aqueous solution is cooled at a rate of about 0.1° C. to about 5° C. per minute.

9. The process of claim 7 wherein the aqueous solution is cooled at a rate of about 0.1° C. to about 2° C. per minute.

10. The process of claim 9 wherein the solvent is isopropanol.

11. The process of claim 7 wherein the aqueous solution is heated to about 60° C.

12. The process of claim 11 wherein the aqueous solution cooled to about 25° C. in about 2 hours.

13. The process of claim 12 wherein the solvent is isopropanol.

14. The process of claim 11 wherein the aqueous solution is maintained at about 60° C. for about 4 hours then cooled to about 25° C. in about 2 hours.

15. The process of claim 14 wherein the solvent is isopropanol.

16. A pharmaceutical composition comprising 3-pyridyl-1-hydroxyethlidene-1,1-bisphosphonic acid sodium wherein the 3-pyridyl-1-hydroxyethlidene-1,1-bisphosphonic acid sodium is from about 50% to about 100% hemipentahydrate and from about 50% to about 0% monohydrate.

17. The pharmaceutical composition of claim 16 wherein the 3-pyridyl-1-hydroxyethlidene-1,1-bisphosphonic acid sodium is from about 80% to about 100% hemipentahydrate and from about 20% to about 0% monohydrate.

18. The pharmaceutical composition of claim 16 wherein the 3-pyridyl-1-hydroxyethlidene-1,1-bisphosphonic acid sodium is from about 90% to about 100% hemipentahydrate and from about 10% to about 0% monohydrate.

* * * * *

UNITED STATES PATENT AND TRADEMARK OFFICE
CERTIFICATE OF CORRECTION

PATENT NO.    : 6,410,520 B2
DATED         : June 25, 2002
INVENTOR(S)   : Frederick Dana Cazer et al.

It is certified that error appears in the above-identified patent and that said Letters Patent is hereby corrected as shown below:

Column 4,
Line 30, delete "n" and insert -- in --.

Column 7,
Line 3, delete "nitrites" and insert -- nitriles --.

Signed and Sealed this

Twenty-fourth Day of August, 2004

JON W. DUDAS
*Director of the United States Patent and Trademark Office*